(12) United States Patent
Han et al.

(10) Patent No.: US 11,193,063 B2
(45) Date of Patent: Dec. 7, 2021

(54) COMPOUND, LIQUID CRYSTAL COMPOSITION AND PHOTOELECTRIC DISPLAY DEVICE THEREOF

(71) Applicant: Jiangsu Hecheng Display Technology Co., Ltd., Yangzhong (CN)

(72) Inventors: Wenming Han, Yangzhong (CN); Wenqi Zhang, Yangzhong (CN); Wenyang Ma, Yangzhong (CN); Zhaoyuan Chen, Yangzhong (CN)

(73) Assignee: Jiangsu Hecheng Display Technology Co., Ltd., Yangzhong (CN)

( * ) Notice: Subject to any disclaimer, the term of this patent is extended or adjusted under 35 U.S.C. 154(b) by 0 days.

(21) Appl. No.: 16/861,320

(22) Filed: Apr. 29, 2020

(65) Prior Publication Data
US 2020/0255738 A1    Aug. 13, 2020

Related U.S. Application Data

(63) Continuation-in-part of application No. PCT/CN2018/116355, filed on Nov. 20, 2018.

(30) Foreign Application Priority Data

Nov. 23, 2017   (CN) .......................... 201711184243.5

(51) Int. Cl.
  *C09K 19/34* (2006.01)
  *C07D 319/06* (2006.01)
  *C09K 19/44* (2006.01)

(52) U.S. Cl.
  CPC ........ *C09K 19/3402* (2013.01); *C07D 319/06* (2013.01); *C09K 19/44* (2013.01); *C09K 2019/3422* (2013.01)

(58) Field of Classification Search
  CPC .... C09K 19/3402; C09K 19/44; C09K 19/04; C09K 2019/3422; C09K 2019/0466; C09K 2019/123; C09K 2019/3004; C09K 2019/301; C09K 2019/3016; C07D 319/06
  See application file for complete search history.

(56) References Cited

U.S. PATENT DOCUMENTS

| | | |
|---|---|---|
| 585,827 A | 7/1897 | Meskill |
| 5,858,270 A | 1/1999 | Matsui et al. |
| 5,858,272 A | 1/1999 | Haseba et al. |
| 5,879,585 A | 3/1999 | Miyazawa et al. |
| 6,051,288 A | 4/2000 | Kondo et al. |
| 6,235,355 B1 | 5/2001 | Haseba et al. |
| 9,657,230 B2 * | 5/2017 | Okumura ............ C09K 19/3458 |
| 10,144,871 B2 | 12/2018 | Furusato et al. |
| 2011/0180756 A1 | 7/2011 | Goto et al. |
| 2016/0280996 A1 | 9/2016 | Okumura et al. |
| 2016/0304784 A1 | 10/2016 | Haseba et al. |
| 2018/0022999 A1 | 1/2018 | Ookawa |

FOREIGN PATENT DOCUMENTS

| | | |
|---|---|---|
| CN | 1158602 A | 9/1997 |
| CN | 1182085 A | 5/1998 |
| CN | 1184462 A | 6/1998 |
| CN | 1211978 A | 2/1999 |
| CN | 104371743 A | 2/2015 |
| CN | 105018108 A | 11/2015 |
| CN | 105295955 A | 3/2016 |
| CN | 105542794 A | 5/2016 |
| CN | 105670648 A | 6/2016 |
| CN | 105849232 A | 8/2016 |
| CN | 107189791 A | 9/2017 |
| CN | 107760318 A | 3/2018 |
| CN | 108239550 A | 7/2018 |
| CN | 108659857 A | 10/2018 |
| CN | 108659858 A | 10/2018 |
| WO | WO 2015/056540 A1 | 4/2015 |
| WO | 2016/133035 A1 | 8/2016 |

OTHER PUBLICATIONS

PCT Search Report for PCT/CN2018/116355 with English translation, dated Feb. 12, 2019.

* cited by examiner

*Primary Examiner* — Geraldina Visconti
(74) *Attorney, Agent, or Firm* — Hoffmann & Baron, LLP

(57) ABSTRACT

A compound having the structure of general formula I is useful as a liquid crystal composition and as a photoelectric display device including the liquid crystal composition. The compound having the structure of general formula I is chemically and physically stable, and has higher clearing point, and both large dielectric anisotropy and large optical anisotropy at the same time. The compound having the structure of general formula I is well compatible with other liquid crystal compounds when applied in a liquid crystal composition, the composition has good stability especially in a low-temperature environment, the characteristic of fast response and a wide range of applicabilities, especially applicable to the IPS-type and TN-TFT-type liquid crystal display devices.

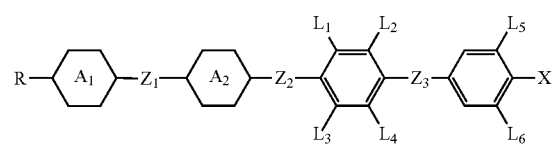

20 Claims, No Drawings

COMPOUND, LIQUID CRYSTAL COMPOSITION AND PHOTOELECTRIC DISPLAY DEVICE THEREOF

CROSS-REFERENCE TO RELATED APPLICATIONS

This application is a Continuation-In-Part (CIP) Application of International Application No. PCT/CN2018/116355, filed Nov. 20, 2018, which claims the benefit of Chinese Application No. 201711184243.5, filed Nov. 23, 2017, the contents of all which are incorporated by reference herein.

TECHNICAL FIELD

The present invention relates to the field of liquid crystal material, particularly to a compound and liquid crystal composition and photoelectric display device thereof.

BACKGROUND ARTS

Liquid crystal display elements using a liquid crystal composition are widely used in displays such as clocks, calculators, word processors, and the like. These liquid crystal display elements take advantage of optical anisotropy, dielectric anisotropy, and the like of a liquid crystal compound. The known operating modes of liquid crystal display elements are mainly classified into the types of PC (phase change), TN (twist nematic), STN (super twisted nematic), ECB (electrically controlled birefringence), OCB (optically compensated bend), IPS (in-plane switching), VA (vertical alignment), and the like. In recent years, studies on applying an electric field to an optically isotropic liquid crystal phase to exhibit an electric birefringence mode are also prevalent.

Based on the driving mode of devices, they are mainly classified into passive matrix (PM), which is classified into the types of static, the multiplex and the like, and active matrix (AM), which is classified into the types of thin film transistor (TFT), metal insulator metal (MIM) and the like.

These liquid crystal display elements comprise liquid crystal compositions having appropriate physical properties. The general physical properties necessary for a liquid crystal compound which is used as a component of a liquid crystal composition are as follows:

(1) chemical stability and physical stability;
(2) high clearing point (liquid crystal phase-isotropy phases transition temperature);
(3) low minimum temperature of the liquid crystal phase (e.g., an optically isotropic liquid crystal phase, such as a nematic phase, a cholesterol phase, a smectic phase and a blue phase, and the like);
(4) excellent compatibility with other liquid crystal compounds;
(5) appropriate dielectric anisotropy;
(6) appropriate optical anisotropy.

When a liquid crystal composition comprising the chemically and physically stable liquid crystal compound as described in (1) is used for a liquid crystal display element, the voltage holding ratio can be improved. In addition, if a liquid crystal composition comprises the liquid crystal compound having high clearing point or low minimum temperature of the liquid crystal phase as described in (2) and (3), the temperature ranges of nematic phase liquid crystals or optically isotropic liquid crystals can be enlarged, and can be used in a display element in a wide temperature range. In order to show characteristics that are difficult to present via a single liquid crystal compound, a liquid crystal compound is generally mixed with various other liquid crystal compounds to prepare a liquid crystal composition for use. Thus, it is preferable that the liquid crystal compound used in the liquid crystal display element has good compatibility with other liquid crystal compounds and the like as described in (4). In recent years, liquid crystal display elements having higher display performances, such as the characteristics of contrast, display capacity, response time, and the like, have been particularly required, and then there is a demand for a low driving voltage for the liquid crystal composition used. Moreover, in order to drive an optical element driven by an optically isotropic liquid crystal phase at a low voltage, it is best to use a liquid crystal compound having large dielectric anisotropy and optical anisotropy.

SUMMARY OF THE INVENTION

Objects: In view of the defects in the prior art, the object of the present invention is to provide a liquid crystal compound, which is chemically and physically stable, and has higher clearing point, larger dielectric anisotropy, larger optical anisotropy, good low-temperature storage stability and fast response, a liquid crystal composition comprising the liquid crystal compound, and a photoelectric display device comprising the liquid crystal composition.

Technical solutions of the present invention:

In one aspect, the present invention provides a compound having the structure of general formula I:

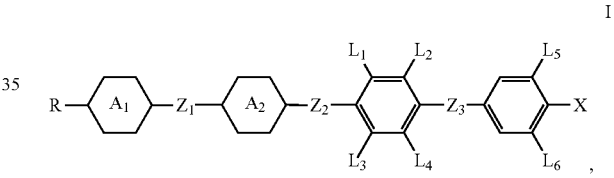

in which,

R represents a $C_{1-18}$ alkyl or a $C_{2-18}$ alkenyl, one or more —$CH_2$— in the alkyl or alkenyl can each be independently replaced by —O— or —CO— in a manner that oxygen atoms are not directly connected, one or more —H in the alkyl or alkenyl can be substituted by halogen or —$CH_3$;

X represents —F, —$OCF_3$ or —$CF_3$;

$L_1$~$L_6$ each independently represents —H or —F;

$Z_1$, $Z_2$ and $Z_3$ each independently represents a single bond, —$CH_2CH_2$—, —$CH_2O$—, —$CF_2O$—, —COO—, —OCO—, —C≡C—, —$OCH_2$—, —$OCF_2$—, —$CF_2CF_2$— or —CH=CH—;

ring

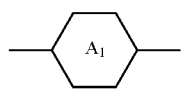

and ring

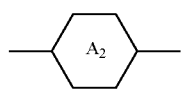

each independently represents

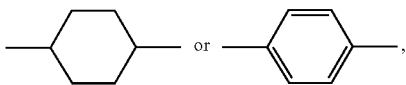

one or more —CH$_2$— in

can be replaced by —O—, and one or more —H on

can be substituted by —F;
at least one of ring

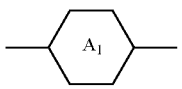

and ring

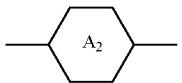

represents

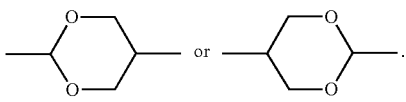

In some embodiments of the present invention, X preferably represents —F or —OCF$_3$.

In some embodiments of the present invention, further preferably, Z$_3$ represents a single bond or —CF$_2$O—.

In some embodiments of the present invention, further preferably, Z$_1$ and Z$_2$ each independently represents a single bond, —CH$_2$CH$_2$—, —CH$_2$O— or —CF$_2$O—.

In some embodiments of the present invention, further preferably, at least one of Z$_1$, Z$_2$ and Z$_3$ is not a single bond.

In some embodiments of the present invention, further preferably, when ring

represents

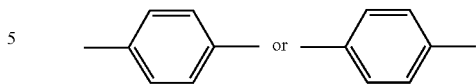

on which —H is substituted by —F, Z$_1$ represents —CH$_2$CH$_2$— or Z$_2$ represents —CF$_2$O—.

In some embodiments of the present invention, preferably, at most four of L$_1$~L$_6$ represents —F.

In some embodiments of the present invention, further preferably, L$_3$ and L$_4$ both represent —H.

In some embodiments of the present invention, preferably, the compound of the present invention is selected from a group consisting of the following compounds:

I-1
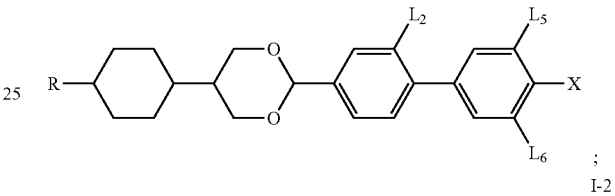

I-2
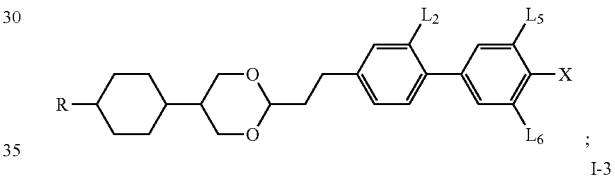

I-3
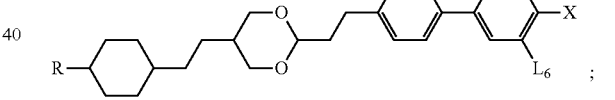

I-4
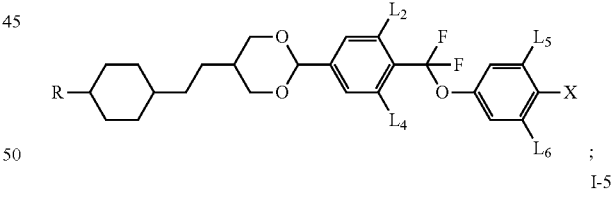

I-5
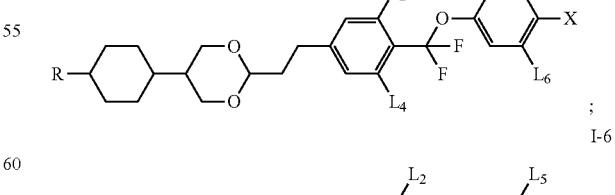

I-6
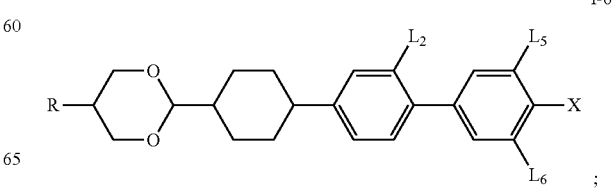

-continued

I-7
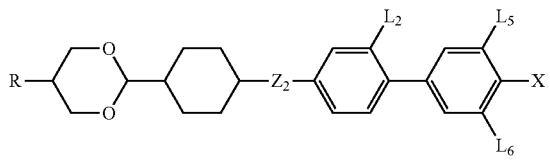

I-8
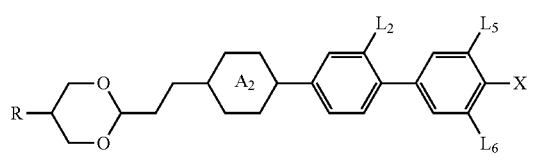

I-9
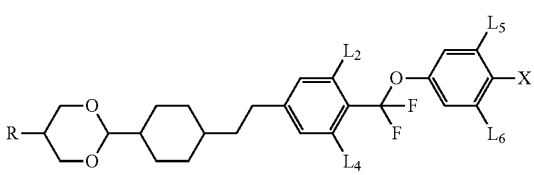

I-10
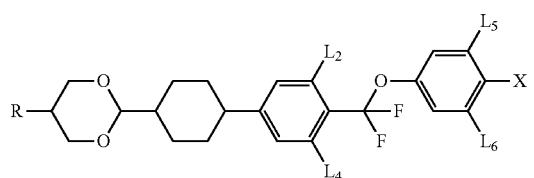

I-11
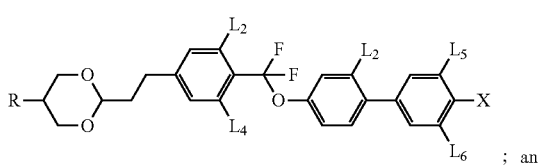; and

I-12
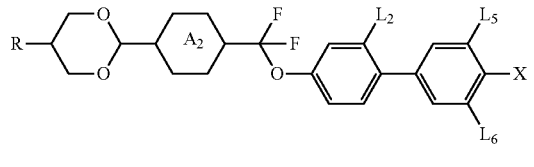, in which,
X represents —F or —OCF$_3$;
ring

represents

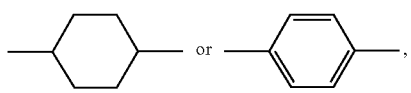, and one or more —H on

can be substituted by —F;
L$_7$ and L$_8$ each independently represents H or F;
Z$_2$ represents —CH$_2$CH$_2$— or —CH$_2$O—.

In some embodiments of the present invention, further preferably, when L$_5$ represents —F, X represents —F.

In some embodiments of the present invention, further preferably, R represents a C$_{1-7}$ chain alkyl or chain alkoxy, or a C$_{2-12}$ chain alkenyl.

The preferred chain alkyl is, for example, methyl, ethyl, n-propyl, isopropyl, n-butyl, isobutyl, sec-butyl, t-butyl, 2-methylbutyl, n-pentyl, sec-pentyl, and the like.

The preferred chain alkoxy is, for example, methoxy, ethoxy, 2-methoxyethoxy, n-propoxy, isopropoxy, n-butoxy, isobutoxy, sec-butoxy, t-butoxy, 2-methylbutoxy, n-pentyloxy, and the like.

The preferred chain alkenyl is, for example, ethenyl, propenyl, butenyl and pentenyl.

In some embodiments of the present invention, further preferably, the compound of present invention is selected from a group consisting of the compounds of general formula I-1, general formula I-2, general formula I-3, general formula I-4, general formula I-5, general formula I-6, general formula I-7, general formula I-8, general formula I-9 and general formula I-11.

In some embodiments of the present invention, still further preferably, the compound of present invention is selected from a group consisting of the compounds of general formula I-1, general formula I-2, general formula I-3, general formula I-4, general formula I-6, general formula I-7, general formula I-8 and general formula I-11.

It should be noted that, simple modifications to chain length of the above compounds also fall into the protection scope of the compounds of the present invention.

The compound of general formula I of the present invention has high clearing point and is useful for the display of the liquid crystal composition constituted thereby at a high temperature; the compound has large dielectric anisotropy and can reduce the driving voltage of liquid crystal display elements; the compound has large optical anisotropy, and the use of this compound can make it easy to control the value of the optical anisotropy of the liquid crystal composition to a desired level.

The compound of general formula I of the present invention is particularly suitable for use in a TFT-type liquid crystal composition as well as various other purposes. For example, there are liquid crystal compositions for use in TN-type, guest-host type, and polymer dispersion type liquid crystal display elements, dynamic dispersion type and STN-type, ferroelectric liquid crystal compositions, anti-ferroelectric liquid crystal compositions, and liquid crystal compositions for use in in-plane switching type, OCB-type and R-OCB-type.

In another aspect, the present invention further provides a liquid crystal composition comprising:
at least one compound of general formula I above;
at least one compound selected from a group consisting of the compounds of general formulas II-1~II-4

II-1
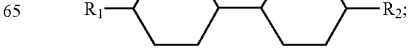

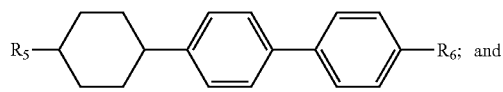
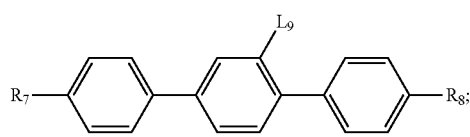

at least one compound selected from a group consisting of the compounds of general formula III-1 and general formula III-2

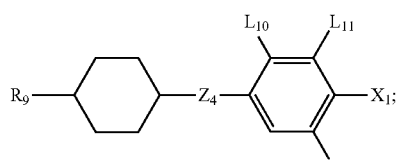

in which, $R_1$, $R_2$, $R_3$, $R_4$, $R_5$, $R_6$, $R_7$, $R_9$ and $R_{10}$ each independently represents a $C_{1-7}$ alkyl or alkoxy, or a $C_{2-7}$ alkenyl or alkenoxy;

$R_8$ represents —F, a $C_{1-7}$ alkyl or alkoxy, or a $C_{2-7}$ alkenyl or alkenoxy;

$L_9$~$L_{12}$ each independently represents —H or —F;

$X_1$ represents —F, a $C_{1-18}$ alkyl or a $C_{2-18}$ alkenyl, one or more —$CH_2$— in the alkyl or alkenyl can each be independently replaced by —O— in a manner that oxygen atoms are not directly connected, one or more —H in the alkyl or alkenyl can be substituted by halogen, and when $X_2$ represents alkyl or alkenyl, or, when one or more —$CH_2$— in the alkyl or alkenyl each is independently replaced by —O— in a manner that oxygen atoms are not directly connected, at least one of $L_{10}$~$L_{12}$ represents —F;

ring

represents

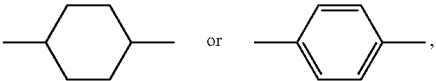

one or more —$CH_2$— in

can be replaced by —O—, and one or more —H on

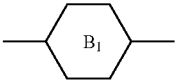

can be substituted by —F;

$Z_4$ and $Z_5$ each independently represents a single bond, —$CH_2CH_2$—, —$CH_2O$—, —$CF_2O$—, —$OCH_2$— or —$OCF_2$—;

n represents 1 or 2, and when n represents 2, ring

can be same or different, and $Z_4$ can be same or different.

In some embodiments of the present invention, preferably, the compound of general formula I is selected from the group consisting of the compounds of general formulas I-1~I-12 above.

In some embodiments of the present invention, further preferably, the compound of general formula I provides 1-50% of the total weight of the liquid crystal composition, the compound selected from the group consisting of the compounds of general formulas II-1~II-4 provides 5-75% of the total weight of the liquid crystal composition, and the compound selected from the group consisting of the compounds of general formula III-1 and general formula III-2 provides 1-50% of the total weight of the liquid crystal composition.

In some embodiments of the present invention, further preferably, the liquid crystal composition comprises at least one compound selected from a group consisting of the compounds of general formula II-1-a and general formula II-1-b:

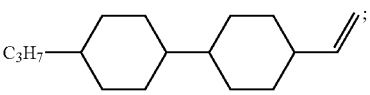

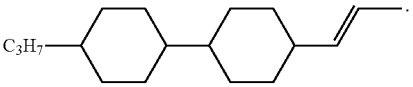

In some embodiments of the present invention, further preferably, the liquid crystal composition comprises at least one compound selected from a group consisting of the compounds of general formulas II-2~II-4.

In some embodiments of the present invention, further preferably, in the compound selected from the group consisting of the compounds of general formula III-1 and general formula III-2, $L_{10}$ and $L_{11}$ represent —F, and $L_{12}$ represents —H.

In some embodiments of the present invention, further preferably, the compound selected from the group consisting of the compounds of general formula II-1-a and general formula II-1-b provides 5-65% of the total weight of the liquid crystal composition, the compound selected from the group consisting of the compounds of general formulas II-2~II-4 provides 5-45% of the total weight of the liquid crystal composition, and the compound selected from the group consisting of the compounds of general formula III-1 and general formula III-2 provides 1-35% of the total weight of the liquid crystal composition.

In some embodiments of the present invention, preferably, $X_1$ and $X_2$ each independently represents —F, —$CF_3$ or —$OCF_3$.

In some embodiments of the present invention, preferably, $Z_4$ and $Z_5$ each independently represents a single bond, —$CH_2CH_2$—, —$CH_2O$— or —$OCH_2$—.

In some embodiments of the present invention, preferably, the compound of general formula III-1 can be selected from a group consisting of the following compounds:

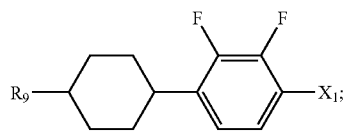

III-1-1

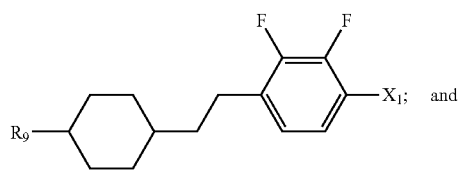

III-1-2

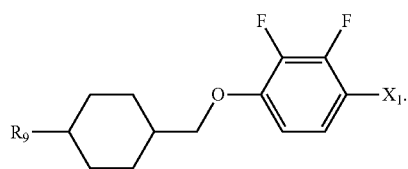

III-1-3

In some embodiments of the present invention, the compound of general formula III-1 can further be selected from a group consisting of the following compounds:

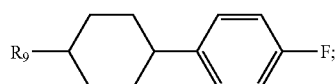

III-1-4

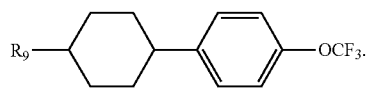

III-1-5

In some embodiments of the present invention, preferably, the compound of general formula III-2 can be selected from a group consisting of the following compounds:

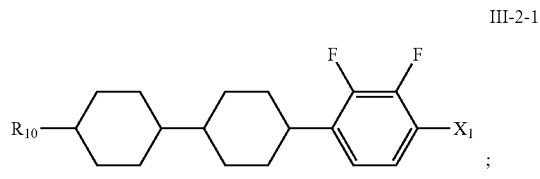

III-2-1

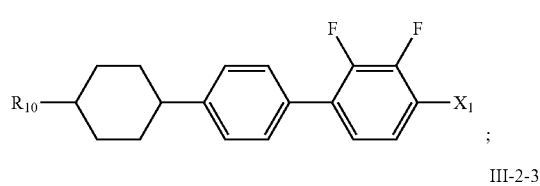

III-2-2

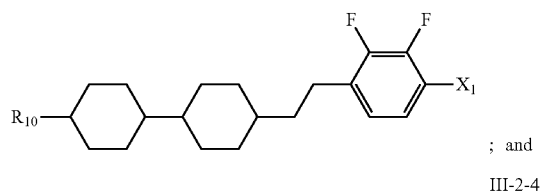

III-2-3

; and

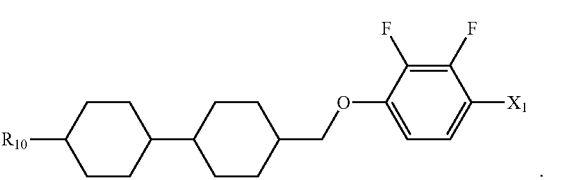

III-2-4

In some embodiments of the present invention, the compound of general formula III-2 can further be selected from a group consisting of the following compounds:

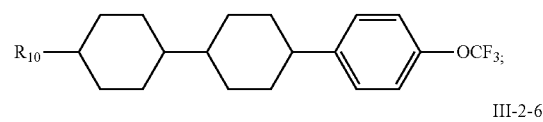

III-2-5

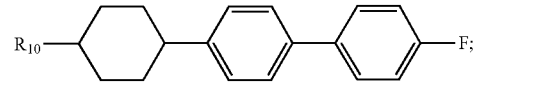

III-2-6

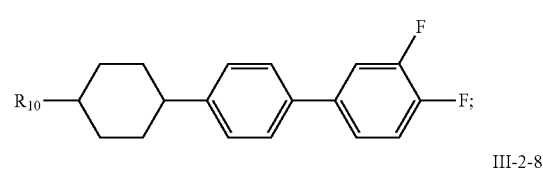

III-2-7

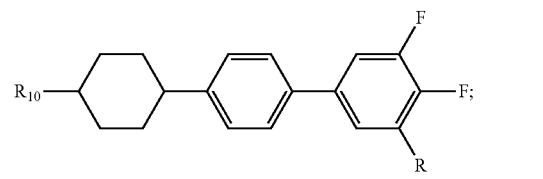

III-2-8

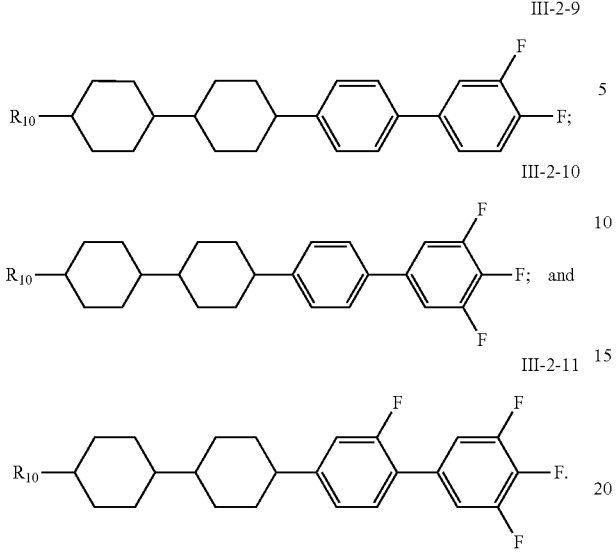

In some embodiments of the present invention, the compound of general formula III-1 is preferably selected from a group consisting of the compounds of general formula III-1-1, general formula III-1-3 and general formula III-1-5.

In some embodiments of the present invention, the compound of general formula III-2 is preferably selected from a group consisting of the compounds of general formula III-2-2, general formula III-2-4, general formula III-2-5, general formula III-2-6, general formula III-2-8, general formula III-2-10 and general formula III-2-11.

In still another aspect, the present invention further provides a photoelectric display device comprising the liquid crystal composition above.

Beneficial Effects:

The compound having the structure of general formula I provided by the present invention is chemically and physically stable, and has higher clearing point, and both large dielectric anisotropy and large optical anisotropy at the same time. The compound having the structure of general formula I of the present invention is well compatible with other liquid crystal compounds when applied in a liquid crystal composition, the composition has good stability especially in a low-temperature environment, the characteristic of fast response and a wide range of applicabilities, especially applicable to the IPS-type and TN-TFT-type liquid crystal display devices.

DETAILED EMBODIMENTS

The present invention will be illustrated by combining the detailed embodiments below. It should be noted that, the following Examples are exemplary embodiments of the present invention, which are only used to illustrate the present invention, not to limit it. Other combinations and various modifications within the conception of the present invention are possible without departing from the subject matter and scope of the present invention.

For the convenience of the expression, the group structures of the liquid crystal compositions in the following Examples are represented by the codes listed in Table 1:

TABLE 1

Codes of the group structures of liquid crystal compounds

| Unit structure of group | Code | Name of group |
|---|---|---|
|  | C | 1,4-cyclohexylidene |
|  | D | 1,3-dioxane-2,5-diyl |
|  | P | 1,4-phenylene |
|  | G | 2-fluoro-1,4-phenylene |
|  | U | 2,5-difluoro-1,4-phenylene |
|  | W | 2,3-difluoro-1,4-phenylene |
| —CH$_2$CH$_2$— | 2 | ethyl bridge bond |
| —OCF$_3$ | OCF3 | trifluoromethoxy |
| —F | F | fluorine substituent |
| —O— | O | oxygen substituent |
| —CF$_2$O— | 1(2F) or Q | difluoro ether group |
| —CH$_2$O— | 1O | methyleneoxy |
| —COO— | E | ester bridge bond |
| —C$_n$H$_{2n+1}$ or —C$_m$H$_{2m+1}$ | n or m | alkyl |
| —CH=CH— or —CH=CH$_2$ | V | ethenyl |

Taking a compound with the following structural formula as an example:

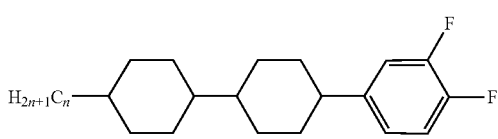

Represented by the codes listed in Table 1, this structural formula can be expressed as nCCGF, in which, n in the code represents the number of the carbon atoms of the alkyl on the left, for example, n is "3", meaning that the alkyl is —C$_3$H$_7$; C in the code represents cyclohexyl, G represents 2-fluoro-1,4-phenylene, and F represents fluoro.

The abbreviated codes of the test items in the following Examples are as follows:

Cp (° C.) clearing point (nematic-isotropy phases transition temperature)

Δn optical anisotropy (589 nm, 25° C.)

Δε dielectric anisotropy (1 KHz, 25° C.)

$\tau_{off}$ the time required to reduce the transmittance from 90% to 10% when removing the electric field (ms, 25° C.)

t−30° C. low-temperature storage time (at −30° C.)

In which, the optical anisotropy is tested using an Abbe Refractometer under a sodium lamp (589 nm) light source at 25° C.;

$\Delta\varepsilon = \varepsilon_{\parallel} - \varepsilon_{\perp}$, in which, $\varepsilon_{\parallel}$ is a dielectric constant parallel to the molecular axis, $\varepsilon_{\perp}$ is a dielectric constant perpendicular to the molecular axis, with the test conditions: 25° C., 1 KHz, a TN90-type test cell with a cell gap of 7 μm.

The test conditions of $\tau_{off}$: an IPS-type test cell with a cell gap of 3.5 μm, 5 V, and a DMS505 tester.

The compound of general formula I of the present invention may be prepared by conventional organic synthesis methods. The methods for introducing a target terminal group, a cyclic group, and a linking group into a starting material can be found in the following literatures: Organic Synthesis (John Wiley & Sons Inc.), Organic Reactions (John Wiley & Sons Inc.), Comprehensive Organic Synthesis (Pergamon Press), and the like.

The methods for generating linking groups $Z_1$, $Z_2$ and $Z_3$ in a compound of general formula I can refer to the following schemes, wherein $MSG^1$ or $MSG^2$ is a monovalent organic group having at least one ring, and a plurality of $MSG^1$ (or $MSG^2$) used in the following schemes can be the same or different.

(1) Synthesis of Single Bond

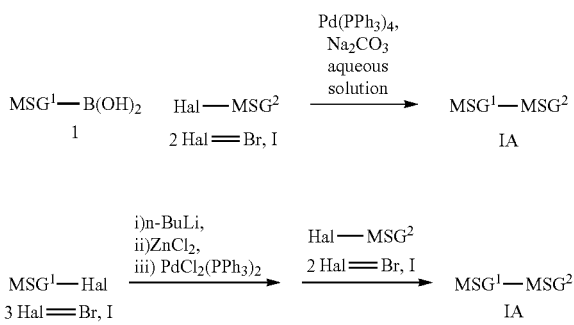

Compound (1A) with a single bond is prepared by allowing an aryl boronic acid (21) to react, in the presence of an aqueous carbonate solution and a catalyst such as tetrakis(triphenylphosphine)palladium, with compound (2) prepared according to a well-known method. Compound (1A) may also prepared by allowing compound (3) prepared according to a well-known method to react with n-butyllithium and subsequently with zinc chloride, and further with compound (2) in the presence of a catalyst such as dichlorobis(triphenylphosphine)palladium.

(2) Synthesis of —COO— and —OCO—

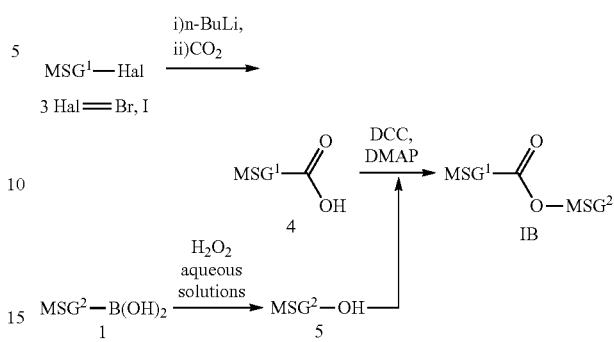

A carboxylic acid (4) is obtained by allowing compound (3) to react with n-butyllithium and then with carbon dioxide. In the presence of 1,3-dicyclohexylcarbodiimide (DCC) and 4-dimethylaminopyridine (DMAP), compound (4) and phenol (5) synthesized by a well-known method are dehydrated to synthesize compound (IB) having —COO—. A compound having —OCO— can also be synthesized by this method.

(3) Synthesis of —CF₂O— and —OCF₂—

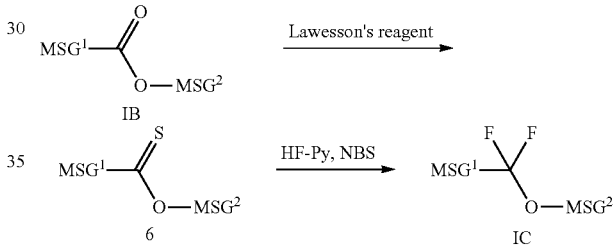

Compound (6) is obtained by treating compound (1B) with a thiation agent such as Lawesson's reagent. Compound (1C) having —CF₂O— is prepared by fluorinating compound (6) with a hydrogen fluoride-pyridine and N-bromosuccinimide (NBS) (refer to M. Kuroboshi et al., Chem. Lett., 1992, 827). Compound (1C) having —CF₂O— may also be prepared by fluorinating compound (6) with (diethylamino)sulfur trifluoride (DAST) (refer to W. H. Bunnelle et al., J. Org. Chem. 1990, 55, 768). A compound having —CF₂O— may also be synthesized according to the method.

(4) Synthesis of —CH=CH—

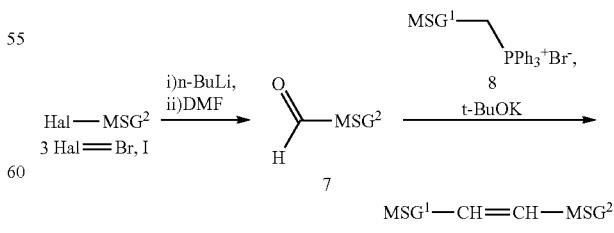

Aldehyde (7) is obtained by allowing the compound (3) to react with n-butyllithium and then with formamide such as N,N-dimethylformamide (DMF). Compound (1D) is prepared by allowing phosphorus ylide, which is generated by reacting a phosphonium salt (8) prepared according to a well-known method with potassium t-butoxide, to react with aldehyde (7). A cis isomer is generated depending on reaction conditions, and therefore the cis isomer may be isomerized into a trans isomer according to a well-known method, when necessary.

(5) Synthesis of —CH$_2$CH$_2$—

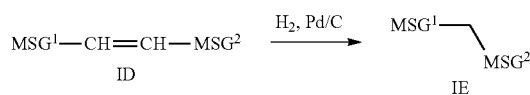

Compound (1E) may be prepared by hydrogenating compound (1D) with a catalyst such as palladium on carbon.

(6) Synthesis of —CH$_2$O— or —OCH$_2$—

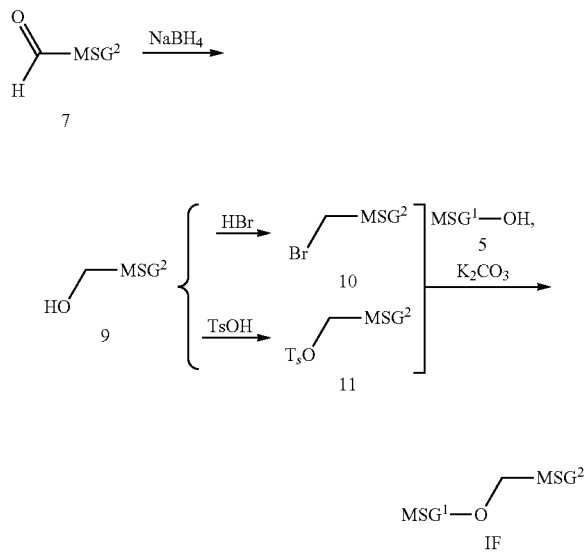

Compound (9) is obtained by reducing compound (7) with sodium boron hydride. Compound (10) is obtained by halogenating compound (9) with hydrobromic acid. Alternatively, compound (11) is obtained by protecting the hydroxyl group of compound (9) with p-toluenesulfonic acid. Compound (1F) is prepared by allowing compound (10) or compound (11) to react with compound (5) in the presence of potassium carbonate. A compound having —OCH$_2$— may also be synthesized according to these methods.

For rings such as 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5,6-tetrafluoro-1,4-phenylene and the like, the starting materials are already commercially available or their synthesis methods are well-known.

The preferred synthetic methods of representative compounds are illustrated below.

Example 1

Synthesis of compound I-1 (R=—C$_3$H$_7$, L$_2$=—H, L$_5$=L$_6$=X=—F):

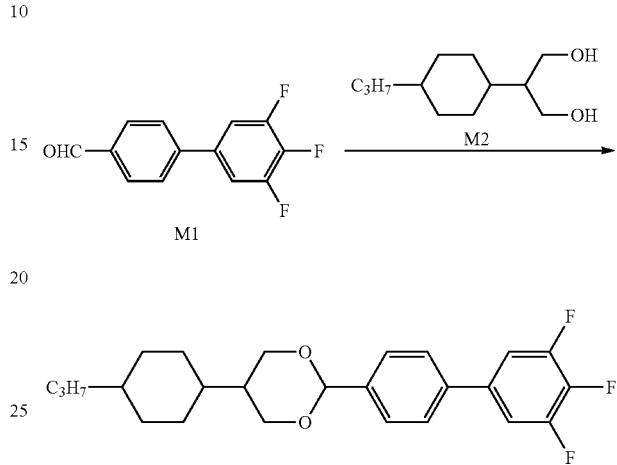

I-1
(R = -C$_3$H$_7$, L$_2$ = -H, L$_5$ = L$_6$ = X = -F)

The specific preparation process is as follows:

To a 500 mL three-necked flask are added 2.4 g compound M1, 2 g compound M2, 150 mL toluene, and 0.05 g p-toluenesulfonic acid, and the mixture is heated under reflux and watershed for 3 h. After the reaction is completed, it is post-treated and purified via recrystallization and column chromatography to obtain 2.2 g white solid (GC>99%, yield: 53%).

MS: 207(24%), 236(80%), 418(100%).

According to the synthetic method of compound I-1 (R=—C$_3$H$_7$, L$_2$=—H, L$_5$=L$_6$=X=—F), other compounds of general formula I-1, the compounds of general formula I-2, general formula I-3, general formula I-6 and general formula I-8, and the compound of general formula I-7 (Z$_2$ is —CH$_2$CH$_2$—) can be synthesized separately by the simple replacement of compounds M1 and/or M2 (not repeated here).

Example 2

Synthesis of compound I-2 (R=—C$_3$H$_7$, L$_2$=—H, Z$_2$=—CH$_2$CH$_2$—, L$_5$=L$_6$=X=—F):

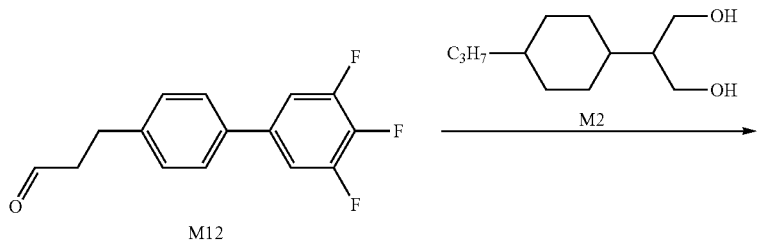

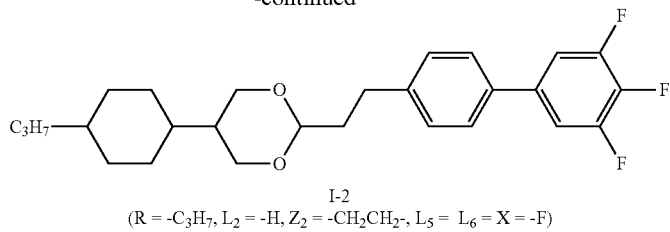

I-2
(R = -C$_3$H$_7$, L$_2$ = -H, Z$_2$ = -CH$_2$CH$_2$-, L$_5$ = L$_6$ = X = -F)

The specific preparation process is as follows:

To a 500 mL three-necked flask are added 2.6 g compound M12, 2 g compound M2, 150 mL toluene and 0.05 g p-toluenesulfonic acid, and the mixture is heated under reflux and watershed for 3 h. After the reaction is completed, it is post-treated and purified via recrystallization and column chromatography to obtain 1.6 g white solid (GC>99%, yield: 36%).

MS: 211(100%), 221(80%), 238(90%), 264(35%), 446 (15%).

Example 3

Synthesis of compound I-4 (R=—C$_3$H$_7$, L$_2$=L$_4$=—F, L$_5$=L$_6$=—H, X=—OCF$_3$):

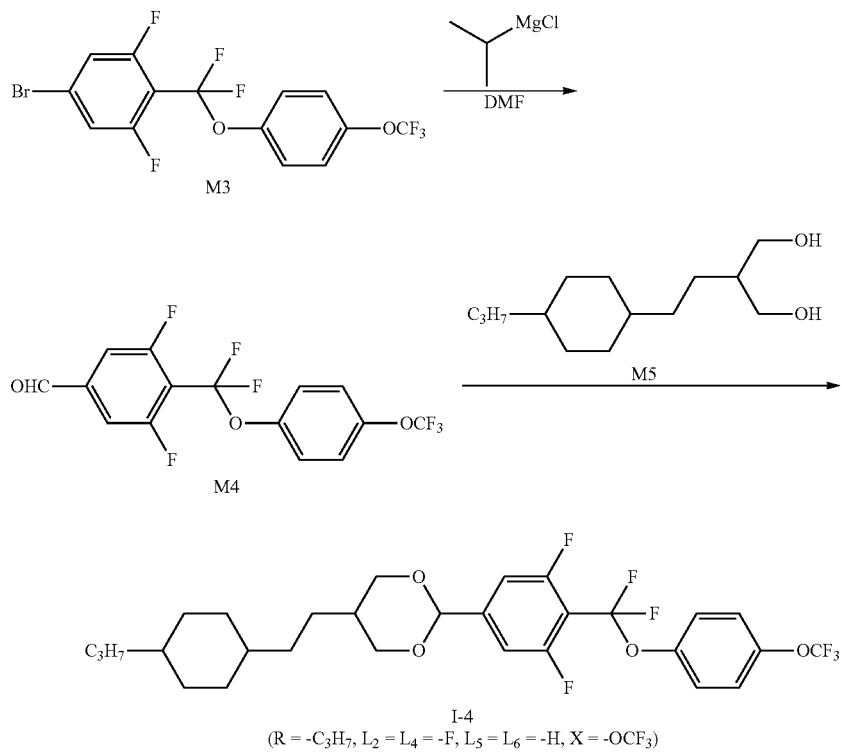

I-4
(R = -C$_3$H$_7$, L$_2$ = L$_4$ = -F, L$_5$ = L$_6$ = -H, X = -OCF$_3$)

The specific preparation process is as follows:

(1) Synthesis of Compound M4

To a 500 mL three-necked flask are added 8.4 g compound M3 and 100 mL anhydrous tetrahydrofuran. Under a nitrogen atmosphere, the temperature is lowered to −78° C., 24 mmol isopropylmagnesium chloride in tetrahydrofuran is added dropwise and stirred for 1 h. A mixture of 1.8 g dimethylformamide and 20 mL anhydrous tetrahydrofuran is added dropwise and stirred for 1 h at a controlled temperature of −78° C. After the temperature is naturally raised to −30° C., the reaction solution is poured into a mixture of 5% dilute hydrochloric acid and ice, post-treated, and purified via column chromatography to obtain 6.6 g compound M4 (GC>97%, yield: 90%).

(2) Synthesis of Compound I-4 (R=—C$_3$H$_7$, L$_2$=L$_4$=—F, L$_5$=L$_6$=—H, X=—OCF$_3$)

To a 500 mL three-necked flask are added 3.7 g compound M4, 2.3 g compound M5, 200 mL dichloromethane and 0.05 g p-toluenesulfonic acid, and the mixture is heated under reflux for 4 h. After the reaction is completed, it is post-treated and purified via recrystallization and column chromatography to obtain 2.4 g white solid (GC>99%, yield: 42%).

MS: 162(15%), 191(87%), 401(100%), 578(12%).

According to the synthetic method of compound I-4 (R=—C$_3$H$_7$, L$_2$=L$_4$=—F, L$_5$=L$_6$=—H, X=—OCF$_3$), other compounds of general formula I-4 and the compound of general formula I-5 can be synthesized separately by the simple replacement of compounds M3 and/or M5 (not repeated here).

Example 4

Synthesis of Compound I-7 (R=—C$_2$H$_5$, Z$_2$=—CH$_2$O—, L$_2$=L$_6$=—H, L$_5$=X=—F):

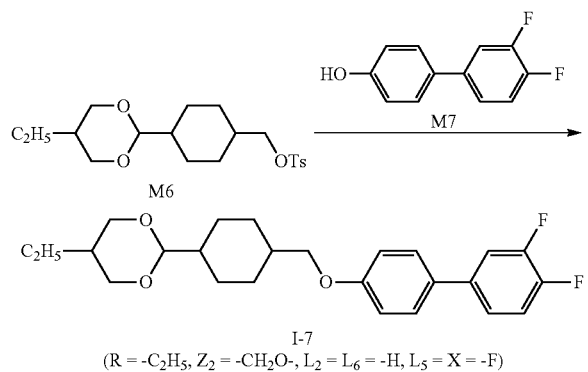

I-7
(R = -C$_2$H$_5$, Z$_2$ = -CH$_2$O-, L$_2$ = L$_6$ = -H, L$_5$ = X = -F)

The specific preparation process is as follows:

To a 500 mL three-necked flask are added 3.8 g compound M6, 2.1 g compound M7, 1.6 g anhydrous potassium carbonate, 0.16 g potassium iodide and 150 ml dimethylformamide, and the mixture is stirred at 90° C. for 5 h. After the reaction is completed, it is post-treated and purified via column chromatography to obtain 2.7 g white solid (GC>99%, yield: 65%).

MS: 115(100%), 206(25%), 416(6%).

According to the synthetic method of compound I-7 (R=—C$_2$H$_5$, Z$_2$=—CH$_2$O—, L$_2$=L$_6$=—H, L$_5$=X=—F), other compounds of general formula I-7 can be synthesized separately by the simple replacement of compounds M6 and/or M7 (not repeated here).

Example 5

Synthesis of Compound I-11 (R=—C$_5$H$_{11}$, L$_2$=—H, L$_5$=L$_6$=L$_7$=L$_8$=X=—F):

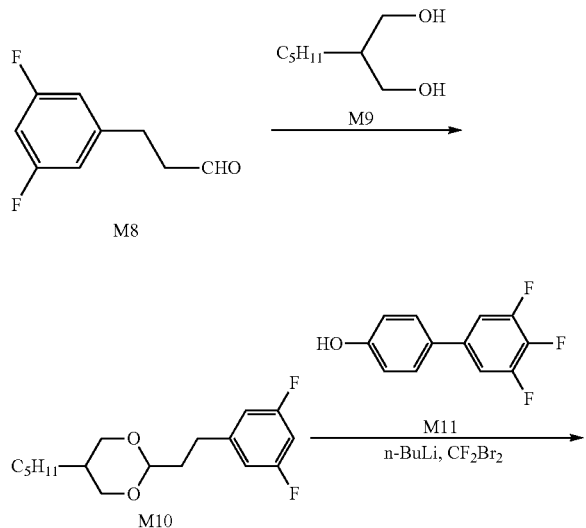

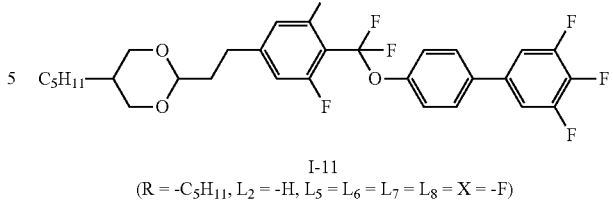

I-11
(R = -C$_5$H$_{11}$, L$_2$ = -H, L$_5$ = L$_6$ = L$_7$ = L$_8$ = X = -F)

The specific preparation process is as follows:

(1) Synthesis of Compound M10

To a 500 mL three-necked flask are added 3.4 g compound M8, 3 g compound M9, 0.1 g p-toluenesulfonic acid and 200 mL toluene, and the mixture is dehydrated under heating and reflux for 3 h. It is post-treated and purified via column chromatography to obtain 5.9 g compound M10 (racemic) (yield: 100%).

(2) Synthesis of Compound I-11 (R=—C$_5$H$_{11}$, L$_2$=—H, L$_5$=L$_6$=L$_7$=L$_8$=X=—F)

To a 500 mL three-necked flask are added 5.9 g compound M10 and 150 mL anhydrous tetrahydrofuran. Under a nitrogen atmosphere, the temperature is lowered to −78° C., 24 mmol n-butyllithium in n-hexane (2.4 mol/L) is added dropwise and stirred for 1 h. A mixture of 5.5 g difluorodibromomethane and 30 mL anhydrous tetrahydrofuran is added dropwise, and after the dropwise addition is completed, the temperature is naturally raised to −20° C. The reaction solution is poured into an ice-water mixture, extracted, separated, washed with water, and evaporated to remove the solvent. To a 250 mL three-necked flask are added the resultant oil together with 4.5 g compound M11, 3.3 g anhydrous potassium carbonate and 100 mL dimethylformamide, and the mixture is stirred at a controlled temperature of 90° C. for 4 h. After the reaction is completed, it is post-treated and purified via recrystallization and column chromatography to obtain 1.6 g white solid (GC>99%, yield: 14%).

MS: 157(100%), 176(77%), 185(92%), 560(2%).

According to the synthetic method of compound I-11 (R=—C$_5$H$_{11}$, L$_2$=—H, L$_5$=L$_6$=L$_7$=L$_8$=X=—F), other compounds of general formula I-11, the compounds of general formula I-9, general formula I-10 or general formula I-12 can be synthesized separately by the simple replacement of compounds M8, M9 and/or M11 (not repeated here).

Example 6

The liquid crystal composition of Example 6 is prepared according to each compound and weight percentage listed in Table 2 and then tested for performance by filling the same between two substrates of a liquid crystal display device. The test data is shown in the Table below:

TABLE 2

| Formulation of the liquid crystal composition and its test performances | | | | |
|---|---|---|---|---|
| Code of component | Code of structure | Content percentage | Test results for the performance parameters | |
| 3CDPUF | I-1 | 3 | Cp | 101 |
| 2DCPUF | I-6 | 3 | Δn | 0.117 |
| 3PGP2 | II-4 | 7 | Δε | 5.1 |
| 3CPP2 | II-3 | 5 | $\tau_{off}$ | 8.2 |
| VCCP1 | II-2 | 10 | t-30° C. | >500 h |

TABLE 2-continued

Formulation of the liquid crystal composition and its test performances

| Code of component | Code of structure | Content percentage | Test results for the performance parameters |
|---|---|---|---|
| 3CCV | II-1-a | 30 | |
| 3CPUF | III-2-8 | 19 | |
| 5CPUF | III-2-8 | 10 | |
| 3CD2PUF | I-2 | 6 | |
| V2CCP1 | II-2 | 7 | |
| Total | | 100 | |

Example 7

The liquid crystal composition of Example 7 is prepared according to each compound and weight percentage listed in Table 3 and then tested for performance by filling the same between two substrates of a liquid crystal display device. The test data is shown in the Table below:

TABLE 3

Formulation of the liquid crystal composition and its test performances

| Code of component | Code of structure | Content percentage | Test results for the performance parameters | |
|---|---|---|---|---|
| 3CDPUF | I-1 | 3 | Cp | 99 |
| 2DCPUF | I-6 | 5 | Δn | 0.09 |
| 3PGPF | II-4 | 1 | Δε | 4.1 |
| 3CPP2 | II-3 | 3 | $\tau_{off}$ | 6.8 |
| 5CCPO2 | II-2 | 5 | t-30° C. | >500 h |
| 3CCV | II-1-a | 50 | | |
| 4CCPOCF3 | III-2-5 | 6 | | |
| 3CCV1 | II-1-b | 10 | | |
| 3CD2PUF | I-2 | 4 | | |
| 3C2DUQPOCF3 | I-4 | 8 | | |
| 3CPPF | III-2-6 | 2 | | |
| 3CCPOCF3 | III-2-5 | 3 | | |
| Total | | 100 | | |

Example 8

The liquid crystal composition of Example 8 is prepared according to each compound and weight percentage listed in Table 4 and then tested for performance by filling the same between two substrates of a liquid crystal display device. The test data is shown in the Table below:

TABLE 4

Formulation of the liquid crystal composition and its test performances

| Code of component | Code of structure | Content percentage | Test results for the performance parameters | |
|---|---|---|---|---|
| 3CDPUF | I-1 | 3 | Cp | 101 |
| 2DCPUF | I-6 | 3 | Δn | 0.1 |
| 3CWO2 | III-1-1 | 5 | Δε | 7.5 |
| 3CPP2 | II-3 | 5 | $\tau_{off}$ | 9 |
| 5PGPF | II-4 | 2 | t-30° C. | >500 h |
| 3CCV | II-1-a | 40 | | |
| 3CPUF | III-2-8 | 3 | | |
| 5CPUF | III-2-8 | 3 | | |
| 3CD2PUF | I-2 | 6 | | |
| 3CCV1 | II-1-b | 2 | | |
| 3C2DUQPOCF3 | I-4 | 8 | | |
| 5D2UQPUF | I-11 | 7 | | |
| 3CCPUF | III-2-10 | 4 | | |
| 4CCPUF | III-2-10 | 4 | | |
| 5CCGUF | III-2-11 | 5 | | |
| Total | | 100 | | |

Example 9

The liquid crystal composition of Example 9 is prepared according to each compound and weight percentage listed in Table 5 and then tested for performance by filling the same between two substrates of a liquid crystal display device. The test data is shown in the Table below:

TABLE 5

Formulation of the liquid crystal composition and its test performances

| Code of component | Code of structure | Content percentage | Test results for the performance parameters | |
|---|---|---|---|---|
| 3CDPUF | I-1 | 3 | Cp | 100 |
| 2DCPUF | I-6 | 3 | Δn | 0.115 |
| 3CC1OWO2 | III-2-4 | 3.5 | Δε | 9.8 |
| 3CPWO4 | III-2-2 | 5 | $\tau_{off}$ | 11.1 |
| VCCP1 | II-2 | 2 | t-30° C. | >500 h |
| 3CCV | II-1-a | 21 | | |
| 3CPUF | III-2-8 | 15 | | |
| 5CPUF | III-2-8 | 15 | | |
| 3CD2PUF | I-2 | 6 | | |
| 3CCV1 | II-1-b | 2 | | |
| 3C2DUQPOCF3 | I-4 | 8 | | |
| 5D2UQPUF | I-11 | 7 | | |
| 2DC1OPGF | I-7 | 4 | | |
| 4D2CPUF | I-8 | 4 | | |
| 3C1OWO1 | III-1-3 | 1.5 | | |
| Total | | 100 | | |

Example 10

The liquid crystal composition of Example 10 is prepared according to each compound and weight percentage listed in Table 6 and then tested for performance by filling the same between two substrates of a liquid crystal display device. The test data is shown in the Table below:

TABLE 6

Formulation of the liquid crystal composition and its test performances

| Code of component | Code of structure | Content percentage | Test results for the performance parameters | |
|---|---|---|---|---|
| 3CDPUF | I-1 | 3 | Cp | 103 |
| 2DCPUF | I-6 | 3 | Δn | 0.122 |
| 3C2D2PUF | I-3 | 5 | Δε | 13 |
| 7CPOCF3 | III-1-5 | 5 | $\tau_{off}$ | 13.7 |
| VCCP1 | II-2 | 5 | t-30° C. | >500 h |
| 3CC2 | II-1 | 10 | | |
| 3CPUF | III-2-8 | 15 | | |
| 5CPUF | III-2-8 | 15 | | |
| 3CD2PUF | I-2 | 6 | | |

TABLE 6-continued

Formulation of the liquid crystal composition and its test performances

| Code of component | Code of structure | Content percentage | Test results for the performance parameters |
|---|---|---|---|
| V2CCP1 | II-2 | 5 | |
| 3C2DUQPOCF3 | I-4 | 8 | |
| 5D2UQPUF | I-11 | 7 | |
| 2DC1OPGF | I-7 | 4 | |
| 4D2CPUF | I-8 | 4 | |
| 4D2UQPUF | I-11 | 5 | |
| Total | | 100 | |

As can be seen from the test data of the above Examples, the liquid crystal composition comprising the compound having the structure of general formula I of the present invention has high clearing point, appropriately high optical anisotropy, higher dielectric anisotropy, good low-temperature storage stability and fast response, and is applicable to the IPS-type and TN-TFT-type liquid crystal display devices.

The Examples illustrated above are merely preferred embodiments of the present invention, and are not intended to limit the present invention in any form. Although the present invention has been disclosed as above with preferred embodiments, it is not intended to limit the present invention. Without departing from the scope of the technical solutions of the present invention, any person skilled in the art should be able to use the disclosed technical contents to make some changes or modifications to obtain equivalent embodiments with equivalent changes. Any simple alterations, equivalent changes and modifications made to the above embodiments according to the technical essence of the present invention without departing from the content of the technical solution of the present invention still fall into the scope of the technical solution of the present invention.

INDUSTRIAL APPLICABILITY

The compound and liquid crystal composition thereof related in the present invention can be applied to the field of liquid crystal.

We claim:
1. A compound having the structure of general formula I:

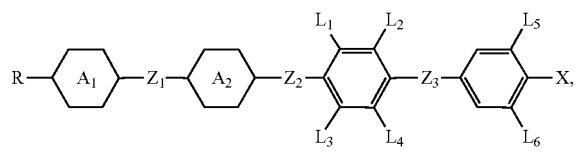

in which,
R represents a $C_{1-18}$ alkyl or a $C_{2-18}$ alkenyl, one or more —$CH_2$— in the alkyl or alkenyl can each be independently replaced by —O— or —CO— in a manner that oxygen atoms are not directly connected, one or more —H in the alkyl or alkenyl can be substituted by halogen or —$CH_3$;
X represents —F, —$OCF_3$ or —$CF_3$;
$L_1$ to $L_6$ each independently represents —H or —F;
$Z_1$, $Z_2$ and $Z_3$ each independently represents a single bond, —$CH_2CH_2$—, —$CH_2O$—, —$CF_2O$—, —COO—, —OCO—, —C≡C—, —$OCH_2$—, —$OCF_2$—, —$CF_2CF_2$— or —CH=CH—, provided that at least two of $Z_1$, $Z_2$ and $Z_3$ are not a single bond;
ring

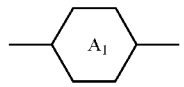

and ring

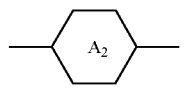

each independently represents

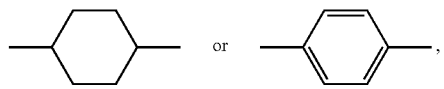

one or more —$CH_2$— in

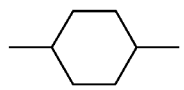

can be replaced by —O—, and one or more —H on

can be substituted by —F;
at least one of ring

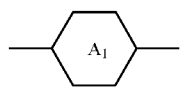

and ring

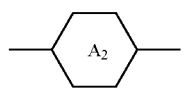

represents

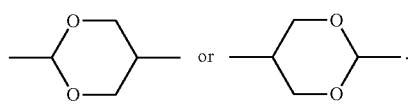

2. The compound according to claim 1, wherein X represents —F or —$OCF_3$.

3. The compound according to claim 2, wherein $Z_3$ represents a single bond or —$CF_2O$—.

4. The compound according to claim 3, wherein $Z_1$ and $Z_2$ each independently represents a single bond, —$CH_2CH_2$—, —$CH_2O$— or —$CF_2O$—.

5. The compound according to claim 4, wherein when ring

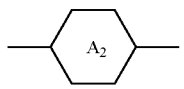

represents

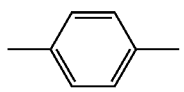

on which —H is substituted by —F, $Z_1$ represents —$CH_2CH_2$— or $Z_2$ represents —$CF_2O$—.

6. The compound according to claim 1, wherein at most four of $L_1$ to $L_6$ represents —F.

7. The compound according to claim 6, wherein $L_3$ and $L_4$ both represent —H.

8. The compound according to claim 1, wherein the compound is selected from a group consisting of the following compounds:

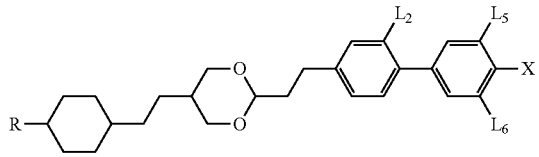
I-3

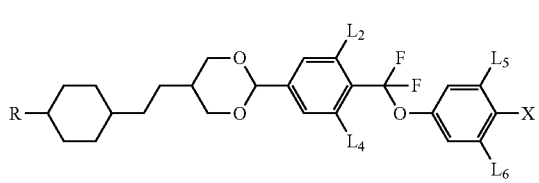
I-4

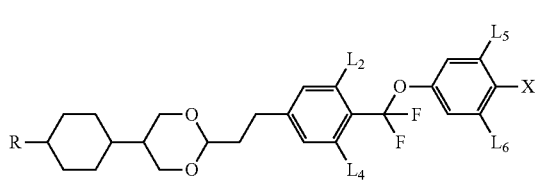
I-5

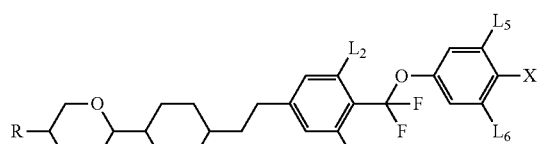
I-9 and

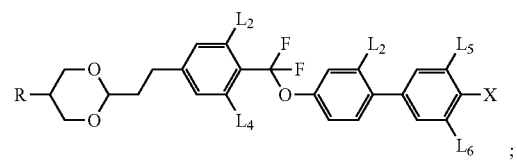
I-11 in which,

X represents —F or —$OCF_3$; and $L_7$ and $L_8$ each independently represents H or F.

9. The compound according to claim 8, wherein when $L_5$ represents —F, X represents —F.

10. A liquid crystal composition, wherein the liquid crystal composition comprises:

at least one compound of general formula I according to claim 1;

at least one compound selected from a group consisting of the compounds of general formulas II-1 to II-4

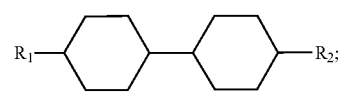
II-1

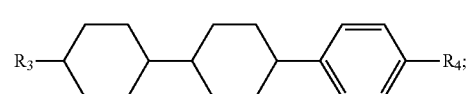
II-2

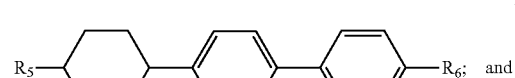
II-3

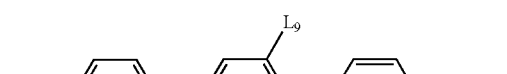
II-4 at least one compound selected from a group consisting of the compounds of general formula III-1 and general formula III-2

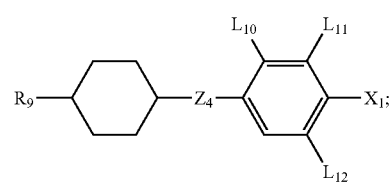
III-1

III-2

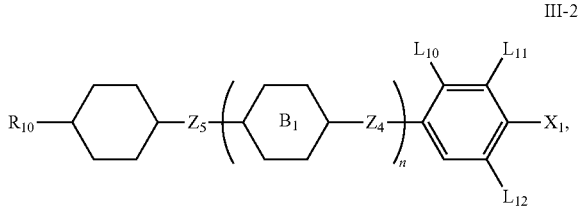

in which,

R₁, R₂, R₃, R₄, R₅, R₆, R₇, R₉ and R₁₀ each independently represents a $C_{1-7}$ alkyl or alkoxy, or a $C_{2-7}$ alkenyl or alkenoxy;

R₈ represents —F, a $C_{1-7}$ alkyl or alkoxy, or a $C_{2-7}$ alkenyl or alkenoxy;

L₉ to L₁₂ each independently represents —H or —F;

X₁ represents —F, a $C_{1-18}$ alkyl or a $C_{2-18}$ alkenyl, one or more —CH₂— in the alkyl or alkenyl can each be independently replaced by —O— in a manner that oxygen atoms are not directly connected, one or more —H in the alkyl or alkenyl can be substituted by halogen, and when X₂ represents alkyl or alkenyl, or, when one or more —CH₂— in the alkyl or alkenyl each is independently replaced by —O— in a manner that oxygen atoms are not directly connected, at least one of L₁₀ to L₁₂ represents —F;

ring

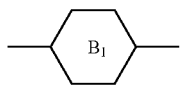

represents

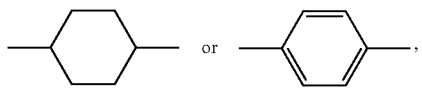

one or more —CH₂— in

can be replaced by —O—, and one or more —H on

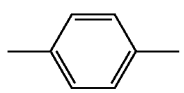

can be substituted by —F;

Z₄ and Z₅ each independently represents a single bond, —CH₂CH₂—, —CH₂O—, —CF₂O—, —OCH₂— or —OCF₂—;

n represents 1 or 2, and when n represents 2, ring

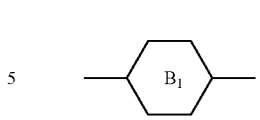

can be same or different, and Z₄ can be same or different.

11. The liquid crystal composition according to claim 9, wherein the compound of general formula I provides 1-50% of the total weight of the liquid crystal composition, the compound selected from the group consisting of the compounds of general formulas II-1 to II-4 provides 5-75% of the total weight of the liquid crystal composition, and the compound selected from the group consisting of the compounds of general formula III-1 and general formula III-2 provides 1-50% of the total weight of the liquid crystal composition.

12. The liquid crystal composition according to claim 11, wherein the liquid crystal composition comprises at least one compound selected from a group consisting of the compounds of general formula II-1-a and general formula II-1-b:

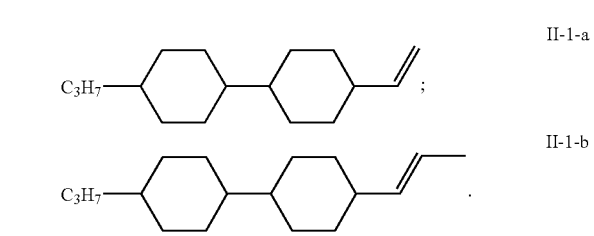

13. The liquid crystal composition according to claim 12, wherein the liquid crystal composition comprises at least one compound selected from a group consisting of the compounds of general formulas II-2 to II-4.

14. The liquid crystal composition according to claim 13, wherein in the compound selected from the group consisting of the compounds of general formula III-1 and general formula III-2, L₁₀ and L₁₁ represent —F, and L₁₂ represents —H.

15. The liquid crystal composition according to claim 13, wherein the compound selected from the group consisting of the compounds of general formula II-1-a and general formula II-1-b provides 5-65% of the total weight of the liquid crystal composition, the compound selected from the group consisting of the compounds of general formulas II-2 to II-4 provides 5-45% of the total weight of the liquid crystal composition, and the compound selected from the group consisting of the compounds of general formula III-1 and general formula III-2 provides 1-35% of the total weight of the liquid crystal composition.

16. A photoelectric display device comprising the liquid crystal composition according to claim 10.

17. A compound having the structure of general formula I-7:

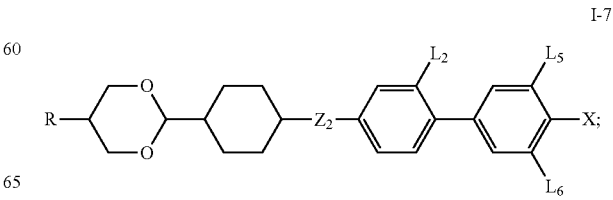

in which,

R represents a $C_{1-18}$ alkyl or a $C_{2-18}$ alkenyl, one or more —$CH_2$— in the alkyl or alkenyl can each be independently replaced by —O— or —CO— in a manner that oxygen atoms are not directly connected, one or more —H in the alkyl or alkenyl can be substituted by halogen or —$CH_3$;

X represents —F or —$OCF_3$; and $L_2$, $L_5$ and $L_6$ each independently represents H or F; and $Z_2$ represents —$CH_2CH_2$— or —$CH_2O$—.

18. A liquid crystal composition, wherein the liquid crystal composition comprises:

at least one compound of general formula I-7 according to claim 17;

at least one compound selected from a group consisting of the compounds of general formulas II-1 to II-4

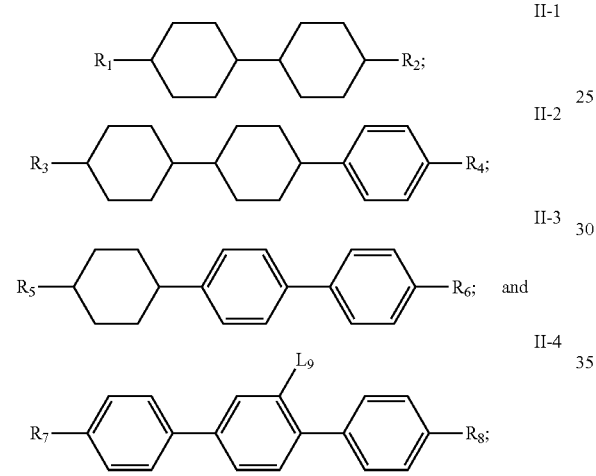

at least one compound selected from a group consisting of the compounds of general formula III-1 and general formula III-2

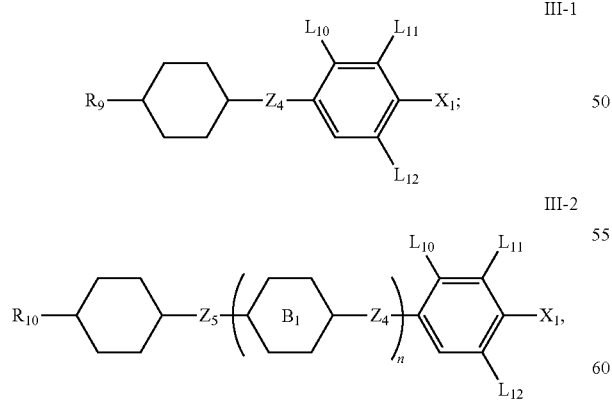

in which, $R_1$, $R_2$, $R_3$, $R_4$, $R_5$, $R_6$, $R_7$, $R_9$ and $R_{10}$ each independently represents a $C_{1-7}$ alkyl or alkoxy, or a $C_{2-7}$ alkenyl or alkenoxy;

$R_8$ represents —F, a $C_{1-7}$ alkyl or alkoxy, or a $C_{2-7}$ alkenyl or alkenoxy;

$L_9$ to $L_{12}$ each independently represents —H or —F;

$X_1$ represents —F, a $C_{1-18}$ alkyl or a $C_{2-18}$ alkenyl, one or more —$CH_2$— in the alkyl or alkenyl can each be independently replaced by —O— in a manner that oxygen atoms are not directly connected, one or more —H in the alkyl or alkenyl can be substituted by halogen, and when $X_2$ represents alkyl or alkenyl, or, when one or more —$CH_2$— in the alkyl or alkenyl each is independently replaced by —O— in a manner that oxygen atoms are not directly connected, at least one of $L_{10}$ to $L_{12}$ represents —F;

ring

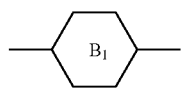

represents

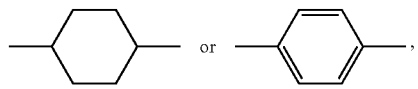

one or more —$CH_2$— in

can be replaced by —O—, and one or more —H on

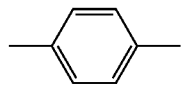

can be substituted by —F;

$Z_4$ and $Z_5$ each independently represents a single bond, —$CH_2CH_2$—, —$CH_2O$—, —$CF_2O$—, —$OCH_2$— or —$OCF_2$—;

n represents 1 or 2, and when n represents 2, ring

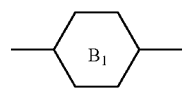

can be same or different, and $Z_4$ can be same or different.

19. The liquid crystal composition according to claim 18, wherein the liquid crystal composition comprises at least one compound selected from a group consisting of the compounds of general formula II-1-a and general formula II-1-b:

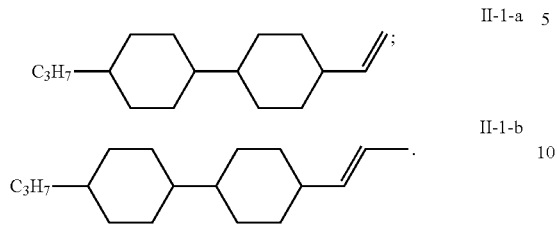

II-1-a

II-1-b

20. The liquid crystal composition according to claim 19, wherein the compound selected from the group consisting of the compounds of general formula II-1-a and general formula II-1-b provides 5-65% of the total weight of the liquid crystal composition, the compound selected from the group consisting of the compounds of general formulas II-2 to II-4 provides 5-45% of the total weight of the liquid crystal composition, and the compound selected from the group consisting of the compounds of general formula III-1 and general formula III-2 provides 1-35% of the total weight of the liquid crystal composition.

* * * * *